(12) United States Patent
Chen et al.

(10) Patent No.: US 8,518,687 B2
(45) Date of Patent: Aug. 27, 2013

(54) CELLULOSE HYDROLASE AND GENE THEREOF

(75) Inventors: Yo-Chia Chen, Neipu Township, Pingtung County (TW); Jeng-Chen Liu, Neipu Township, Pingtung County (TW); Hau-Yu Wang, Tainan (TW); Teng-Chieh Hsu, Taitung (TW); Gia-Luen Guo, New Taipei (TW); Wen-Song Hwang, Longtan Township, Taoyuan County (TW); Jia-Baau Wang, Taipei (TW)

(73) Assignees: National Pingtung University of Science and Technology, Pingtung County (TW); Institute of Nuclear Energy Research, Atomic Energy Council, Executive Yuan, Taoyuan County (TW)

( * ) Notice: Subject to any disclaimer, the term of this patent is extended or adjusted under 35 U.S.C. 154(b) by 0 days.

(21) Appl. No.: 13/424,501

(22) Filed: Mar. 20, 2012

(65) Prior Publication Data

US 2013/0102051 A1    Apr. 25, 2013

(30) Foreign Application Priority Data

Oct. 25, 2011    (TW) .............................. 100138660 A

(51) Int. Cl.
  *C12N 1/20*    (2006.01)
  *C12N 15/00*    (2006.01)
  *C07H 21/04*    (2006.01)

(52) U.S. Cl.
  USPC .................. 435/252.33; 435/320.1; 536/23.2; 536/23.7

(58) Field of Classification Search
  None
  See application file for complete search history.

(56) References Cited

U.S. PATENT DOCUMENTS 6,114,158 A * 9/2000 Li et al. ......................... 435/209

* cited by examiner

*Primary Examiner* — David J Steadman
*Assistant Examiner* — Paul Holland
(74) *Attorney, Agent, or Firm* — Hoffmann & Baron, LLP

(57) ABSTRACT

A cellulose hydrolase and a gene thereof are obtained by screening a cDNA genomic library constructed with *Orpinomyces* sp. Y102. The gene is 1071 base pairs long and comprises an open reading frame (ORF) for producing the cellulose hydrolase comprising 357 amino acids by translation. A transformed cell and a carrier carrying the gene are introduced. The gene is transferred to *E. coli* by transformation, such that *E. coli* can acquire activity of decomposing CMC, beta-glucan, and xylan. The cellulose hydrolase is multifunctional and is capable of decomposing cellubiose and directly decomposing fiber into glucose.

2 Claims, 2 Drawing Sheets

CELLULOSE HYDROLASE AND GENE THEREOF

CROSS-REFERENCE TO RELATED APPLICATION

This non-provisional application claims priority under 35 U.S.C. §119(a) on Patent Application No(s).100138660 filed in Taiwan, R.O.C. on Oct. 25, 2011, the entire contents of which are hereby incorporated by reference.

FIELD OF THE INVENTION

The present invention relates to a segment of cellulose hydrolase gene selected and reproduced from a fungus in a rumen and a protein derived from the segment of cellulose hydrolase gene so as to provide a source whereby the husbandry industry or energy industry produces cellulose hydrolase and a gene thereof.

BACKGROUND OF THE INVENTION

Lignocellulose is essentially composed of cellulose and hemicellulose and is the most abundant natural resource in the nature. Cellulose is insoluble in water, fibrous, and tough. Cellulose is a long-chained substance composed of 10,000 to 15,000 glucose molecules. The glucose molecules of cellulose are linked together by β-1,4 glucosidic bonds, and the β-1,4 glucosidic bonds are bonded to each other by hydrogen bonds, thereby allowing cellulose to take on a close-knit meshy structure. Most creatures, including human beings, are unable to make good use of cellulose-containing substances and use it as a carbon source directly. As a result, the unusable cellulose-containing substances fall within the categories of major sources of wastes, and some of them even pose adverse effects. For example, grains contain lignocellulose which encloses starch and therefore forms aggregates, and in consequence it not only compromises fodder on which poultry and livestock feed but also causes environmental pollution.

Cellulose hydrolase is a collective term that refers to a group of hydrolases which are, through coordinated synergetic effects thereof, capable of converting insoluble cellulose into monosaccharides by hydrolysis such that cellulose can be readily available for use by biological creatures. Depending on the characteristics and mechanism of the enzymes, cellulose hydrolases are of three types. The first type of cellulose hydrolases are known as exo-cellulose hydrolases or cellobiohydrolase. The second type of cellulose hydrolases are known as endo-cellulose hydrolases. The third type of cellulose hydrolases are known as cellobiohydrolase. Cellulose hydrolase-containing additives are added to the fodder to effectively eliminate the nutrient-related barrier caused by cellulose.

In recent years, due to the high speed at which energy resources are exploited and global warming develops, biomass energy is regarded as one of the forms of renewable energy. Take bioethanol as an example, it is added to gasoline to reduce gasoline consumption. Cellulose, a product of polymerization of glucose, is the most abundant organic matter in the world. If cellulose is properly decomposed and utilized, it will not only become a source of a tremendously great amount of biomass energy but also prevent a food crisis which might otherwise arise from keen competition among human beings for foods. Normally, conversion of cellulose into ethanol takes place in three steps, that is, pretreatment, saccharification, and fermentation. Saccharification is aimed at decomposing cellulose into saccharides which can be fermented by microorganism. There are usually two ways of performing saccharification, namely acid hydrolysis and enzyme hydrolysis. Acid hydrolysis not only produces substances, such as furfural and p-hydroxybenzoic acid, which inhibit subsequent fermentation, but is also harmful to an operating worker and the environment. By contrast, enzyme hydrolysis is the preferred option.

Enzyme-based saccharification requires a large amount of cellulose hydrolase. Therefore, cellulose hydrolase accounts for a major cost of bioethanol production. That is to say, a highly efficient cellulose hydrolase is the key to the development of the bioethanol industry. *Orpinomyces* sp. is a cellulose-utilizing strain that draws increasing attention in recent years. Compared with other microorganism present in the rumen, *Orpinomyces* sp. is of the least quantity; for example, *Orpinomyces* sp. accounts for 8% of the microorganism in the rumen of sheep. Nonetheless, *Orpinomyces* sp. is capable of high-efficiency cellulose decomposition. *Orpinomyces* sp. plays a particularly important role when a host feeds on fibrous fodder. In addition to its evolutionary advantages, *Orpinomyces* sp. is proved, by plenty of research results, to be capable of decomposing cellulose by cellulose hydrolase better than frequently used trichoderma fungi by several times to several thousand times. Hitherto, research has shown that absolute anaerobic fungi are capable of decomposing crystalline cellulose better than *Trichoderma reesei* QM9414 fungi widely studied and applied to industrial production. Hitherto, the role played by *Orpinomyces* sp. in the rumen has not yet been directly verified. However, *Orpinomyces* sp. manifests activity of various plant cell wall structure polysaccharide hydrolases in vitro, including exoglucanase, exoglucanase, beta-glucosidase, xylanase, xylosidase, and pectinase. This indicates that *Orpinomyces* sp. is equipped with an encompassing enzymatic system for decomposing plant cell wall structure polysaccharides. In addition to displaying highly specific activity toward a single substrate, plenty of cellulose hydrolases derived from *Orpinomyces* sp. nowadays are multifunction enzymes which not only decompose lignin, β-glucan, and various forms of cellulose, but also efficiently decompose plant residue composed of different constituents.

SUMMARY OF THE INVENTION

In order to enhance utilization of cellulose, the present invention provides a cellulose hydrolase being a protein comprising an amino acid sequence SEQ ID NO:2.

The present invention further provides a cellulose hydrolase. The cellulose hydrolase is a protein manifesting cellulose hydrolase activity and derived by substituting into, removing from, or adding to an amino acid sequence defined in SEQ ID NO:2 one or more amino acids.

The cellulose hydrolase is capable of decomposing fibrous substrates, such as carboxylmethyl cellulose, xylan, and beta-glucan. The cellulose hydrolase manifests activity of decomposing glucose bonds comprising β-1,4 glucosidic bonds by hydrolysis.

The present invention further provides a cellulose hydrolase gene comprising nucleotide sequence SEQ ID NO:1. The present invention further provides a carrier comprising the nucleotide described above. The carrier is deposited at Food Industry Research and Development Institute, Taiwan, with BCRC deposition number BCRC 940643. The present invention further provides a transformed cell comprising the nucleotide described above. The transformed cell is *E. coli*.

The experiment design described below is illustrative, rather than restrictive, of the scope of the present invention.

Reasonable changes which are obvious to persons skilled in the art can be made to the present invention without departing from the scope of the present invention.

BRIEF DESCRIPTION OF THE DRAWINGS

Objectives, features, and advantages of the present invention are hereunder illustrated with specific embodiments in conjunction with the accompanying drawings, in which.

DETAILED DESCRIPTION OF THE PREFERRED EMBODIMENTS

Example 1

According to the present invention, the rumen fluid of a Taiwan's native cow is used as an isolation source, whereas *Orpinomyces* sp. Y102 strain is isolated by the rolling-tube technique and maintained in a culture medium that contains a filter paper Whatman No. 1 functioning as a carbon source. Upon completion of culture, the strain is taken out of the culture medium and evaluated according to the appearance and features of its zoospore and its thallus. The strain is cultured and induced in a culture medium that contains avicel. Upon completion of induction, the strain undergoes total RNA extraction by means of a Trizol agent. Then, a cDNA library is constructed with the strain by performing the steps of mRNA separation, first strand cDNA synthesis, second strand cDNA synthesis, and ligation to a carrier in a way recommended by SMART™ cDNA Library Construction Kit User Manual (BD Biosciences). Afterward, the cDNA library is packaged to λ bacteriophage, and then the bacteriophage is cultured in culture media which contain substrates beta-glucan (90501, Megazyme), xylan (X-0627 Sigma-Aldrich), and carboxylmethyl cellulose (C-5678 Sigma-Aldrich), respectively, and is stained by Congo red, 0379, Amresco, respectively, for screening. Any plaques that features a clear zone is taken out. In vivo excision is performed on *E. coli* BM25.8. The bacteriophage carrier is converted to a plasmid for preservation. The selected gene undergoes sequencing with an automatic sequencer.

Figure 1:
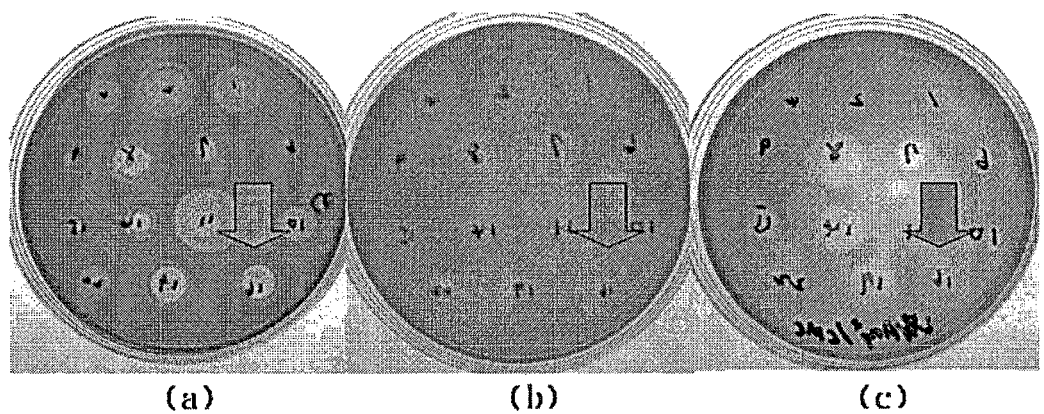
FIG. 1 shows the substrate decomposition capability manifested by cbh16 gene after being transferred to *E. coli*, wherein *E. coli* is cultured in culture media which contain substrates (a) beta-glucan, (b) xylan, and (c) carboxylmethyl cellulose, respectively, and is dyed by Congo red.

The cellobiohydrolase gene thus cloned is named cbh16 gene. The *E. coli* DH5a transferred strain carrying the cbhC16 gene plasmid (pTripIEX2) is implanted on LB/β-glucan agar petri dish, LB/xylan agar petri dish, and LB/CMC agar petri dish, such that it is cultured until after the night, and then dyed by Congo red and destained by 1M NaCl before being observed and screened for a clear zone. The results are shown in FIG. 1(*a*), (*b*) and (*c*). As indicated by the results, the cbhC16 gene-containing *E. coli* is capable of decomposing lignocelluloses constituents, such as β-glucan, xylan, and CMC, thereby indicating that the protein translated by the gene is a multifunction cellulose hydrolase. The result of the sequencing of the cbhC16 gene reveals: the cbhC16 gene comprises a nucleotide sequence displayed by SEQ ID NO:1; the cbhC16 gene is 1071 base pairs long; the cbhC16 gene comprises an open reading frame (ORF) for translating a cellulose hydrolase comprising 357 amino acids; and the translated enzyme molecule is an amino acid sequence displayed by SEQ ID NO:2. The similarity of the ebhC16 genetic sequence and the closest gene (U97154) in the genbank stands at a mere 63%. The similarity of the translated amino acids and the known closest amino acid sequence (AF031934) also stands at a mere 65%.

Example 2

The expression of the cellobiohydrolase (cbhC16) gene of the present invention is carried out by a pET21 system (Novagen). *E. coli* having a plasmid that contains the cbhC16 gene (hereinafter referred to as *E. coli* DH5a) is implanted on Luria-Bertani broth (LB broth) that contains ampicillin (100 µg/mL) and cultured at 37° C. for 16 hours, and then the plasmid is purified by a mini-MTM plasmid DNA Extraction System (Viogene, made in Taiwan), such that the purified plasmid functions as a template source of a subsequent polymerase chain reaction (PCR). In order to have cbhC16 cloned to pET21a, it is necessary to add the EcoR I restriction enzyme cutting site to the forward end of the C16 gene and add the Xho I restriction enzyme cutting site to the reverse end of the C16 gene, wherein the two primers are named Eco-C16-F and Xho-C16-R, respectively. The primer pair, the template, a buffer solution, dNTP, and a polymerase reagent are mixed and put in a thermal cycler for undergoing a preheating process at 95° C. for one minute. Afterward, the preheated mixture undergoes a cycle reaction in 30 instances under the following conditions: at 95° C. for 30 seconds, at 56° C. for 30 seconds, at 72° C. for two minutes, and lastly at 72° C. for five minutes. Upon completion of the cycle reaction, electrophoresis is performed on 5 µL of PCR product with 1% of agar, which is followed by observation and measurement. The PCR product is recycled to undergo hydrolysis by restriction enzymes EcoR I and Xho I, and then a DNA segment that contains the cbhC16 gene is recycled and ligated by T4 ligase (M1804, Promega) to the pET21a (Novagen, USA) incised by the same restriction enzyme. The fully ligated product is transferred to a competent cell (*E. coli* DH5α). Eventually, the inserted segment is confirmed by sequencing, and the constructed expression carrier is named pET21-C16.

The aforesaid pET21-C16 expression carrier is transformed to *E. coli* BL21(DE3). A successfully transformed colony is taken and implanted on 5 ml of LB-Amp broth which contains 100 µg/mL of ampicillin and cultured at 37° C. and 225 rpm for 16 hours by shake culture. The cultured bacterial solution is prepared at a ratio of 1:100, such that 5 mL of the bacterial solution is implanted in 500 mL of fresh LB-Amp broth at 25° C. and 180 rpm by shake culture. IPTG is added to the culture medium as soon as the OD600 of the bacterial solution reaches 0.6-0.8, so as to attain the final concentration of 1 mM. After four hours of induction, the bacterial cells were collected by centrifugation at 4000 g for 20 minutes. The collected cells is suspended in a citrate buffer solution (50 mM, pH6), cracked by ultrasonication, and eventually processed by centrifugation (at 10000 g for 30 minutes) to separate a crude enzyme and pellets. The crude enzyme is purified by columns packed with CM cation resin (10021091, GE Healthcare) and Ni-NTA affinity resin (124118449, QIAGEN), respectively. The purified enzyme undergoes dialysis to remove redundant salts and change the buffer solution.

Figure 2:
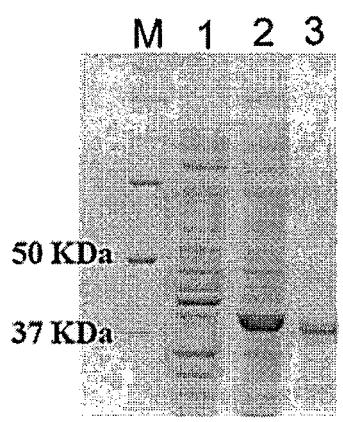
FIG. 2 is a diagram of the result of protein electrophoresis of cbhC16 gene-containing *E. coli* before induction, after induction, and after cbhC16 enzyme purification.

The pET21-C16 is transferred to *E. coli* BL21(DE3) and then undergoes electrophoresis, and the results of electrophoresis before induction, after induction, and after purification are shown in FIG. 2. As shown in FIG. 2, a pre-induction product is denoted by Lane 1, a pro-induction product by Lane 2, and a pro-purification product by Lane 3. The result of FIG. 2 indicates that, upon induction, *E. coli* produces an induced product of 38 KDa approximately, and the induced product is purified by column chromatography using columns packed with ion exchange resin and affinity resin.

Example 3

Upon completion of purification, 40 μl of enzyme and 360 μl of 1% CMC (Sigma) or avicel (Merck) are evenly mixed in a citrate buffer solution (50 mM, pH 6.0) to react at 50° C. for 10 minutes. After the reaction, the dinitrosalicylic acid method (DNS) is employed to measure the quantity of reduced sugar, and then the measured reduced sugar quantity is converted into the activity. One unit (U) of enzyme is defined as 1μ mole of reduced sugar is released by one unit (U) of enzyme per minute. Protein concentration is measured by BCA protein quantification package (Pierce Ltd. USA). The purified product attains a specific activity of 16 U/mg protein with respect to carboxylmethyl cellulose, indicating that an enzyme protein expressed by this segment of gene manifests the activity and function of endocellulose hydrolase (that is, capable of hydrolyzing glucose bonds comprising β-1,4 glucosidic bonds).

Example 4

Figure 3:
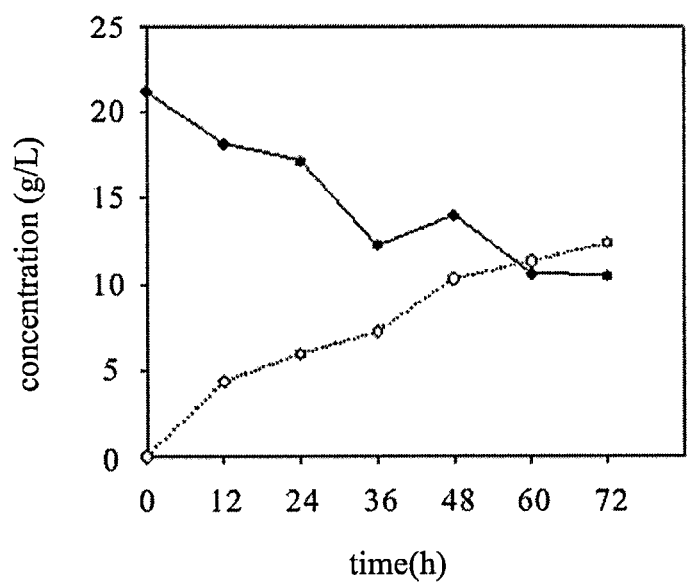
FIG. 3 is a diagram of the result of hydrolysis of cellubiose by cellulose hydrolase (cbhC16) according to the present invention.

The cellulose hydrolase (cbhC16) of the present invention reacts with cellobiose directly, and the result of the reaction is shown in FIG. 3 as follows: cellobiose (indicated by block dots in FIG. 3) decreases continuously as time passes; glucose (indicated by white dots in FIG. 3) in the reaction solution increases continuously as time passes; and cellobiose is decreased and decomposed by at least 50% in 72 hours. The results prove that the cbhC16 enzyme of the present invention is capable of incising cellobiose and thus manifests the activity of cellobiose enzyme.

As indicated by the data of the aforesaid examples, the present invention provides a cellulose hydrolase gene selected *Orpinomyces* sp.Y102. The cellulose hydrolase gene comprises a nucleotide sequence displayed by SEQ ID NO:1. The nucleotide sequence is 1071 base pairs long. The nucleotide sequence can be translated to form an amino acid sequence displayed by SEQ ID NO:2, and 357 amino acids can be obtained by the translation, resulting in a calculated molecular weight of 38.2 KDa.

The present invention is characterized in that sequence comparison reveals: the similarity of the genetic sequence and the closest gene (U97154) stands at a mere 63%; and the similarity of the deduced amino acids and the known closest amino acid sequence (AF031934) stands at a mere 65%, too. Therefore, the gene sequence of the present invention has novelty.

Furthermore, the gene of the present invention is transferred and directly introduced into *E. coli*, such that the *E. coli* is capable of decomposing three substrates, namely carboxylmethyl cellulose, β-glucan, and xylan. Afterward, the gene is embedded in a recombinant protein expression carrier and then transferred to *E. coli* for induced mass production of enzyme protein. The induced and obtained enzyme protein is purified by columns, such that the purified enzyme protein attains a specific activity of 16 U/mg protein with respect to the product carboxylmethyl cellulose. Moreover, a cellobiose hydrolysis test is performed to reveal that cellobiose decreases continuously as time passes, resulting in a cellobiose hydrolysis rate of 50% approximately in 72 hours.

In conclusion, an enzyme protein produced by translation of a cellulose hydrolase gene provided by the present invention is a multifunction cellulose hydrolase.

What is claimed is:

1. An isolated cellulose hydrolase gene comprising the nucleotide sequence of SEQ ID NO: 1.

2. A transformed cell comprising the isolated cellulose hydrolase gene claim 1, wherein the transformed cell is *Escherichia coli*.

* * * * *

SEQUENCE LISTING

<160> NUMBER OF SEQ ID NOS: 2

<210> SEQ ID NO 1
<211> LENGTH: 1071
<212> TYPE: DNA
<213> ORGANISM: Artificial Sequence
<220> FEATURE:
<223> OTHER INFORMATION: Synthetic sequence

<400> SEQUENCE: 1

| | | | | | |
|---|---|---|---|---|---|
| atgcaaaatc | cacaaggaca | acaacaacaa | cagcaacaac | aacaacaaaa | tccaccacag | 60 |
| aataatgcag | gtggaaatgg | aagctctcaa | aatttctttg | ttaatgaaat | atatgctaat | 120 |
| ccaaaattca | ttgaagaaat | tgattcttca | attgcaaaat | tagatggtga | attaaaaggt | 180 |
| aaagccgaaa | aggtcaagag | tgttccaact | gctgtttggt | tagcttggga | aggggctcct | 240 |
| gctgaagttg | aacaacatct | taaagctgcc | ggttctaaaa | ctgttgtttt | cattctttac | 300 |
| atgattccaa | ctcgtgactg | taacagttta | gcttctgctg | gtggtgcttc | aagtcttgaa | 360 |
| acttataagg | ttatattga | tagtatttct | aatactatta | agagctatcc | aagttctaag | 420 |
| gttgttatgg | ttgttgaacc | agatactctt | ggtaatcttg | tcactggtac | tagtgaatcc | 480 |
| tgtaaaacag | ttcacacaat | gcacaagaat | gcattatctt | atgctgttaa | tgtctttggt | 540 |
| gctatgagta | atgttagtgt | ttaccttgat | gctgcccatg | gtaaatggtt | aggtggtgtt | 600 |

```
actgataagg ttgctgctgt tattaaggaa atcttaagta atgctccaaa tggaaaaatt    660
cgtggtgtaa gtactaatgt atctaattat caaccagttg cttctgaata ctcctaccat    720
caaaagcttg cttcttctct ttctgctgtt ggaatttcag atatacattt cattgttgat    780
accggccgta atggtgtcga tattactgaa gcattcagca aaactgaaac ctggtgtaac    840
tttattggta ctggttttgg tgaacgtcca aaaggtaatc caaacccagg tatgccatta    900
ttagatgctt acatgtggct caagactcca ggagaagctg atggttcttc taccggttct    960
agagctgatc cagtttgtgc tcgtgcagat tcacttccag gatccccaga tgctggtcaa   1020
tggttccatg aatatttcgt tcaattatta agaatgctaa accaggcttc                1071
```

<210> SEQ ID NO 2
<211> LENGTH: 357
<212> TYPE: PRT
<213> ORGANISM: Artificial Sequence
<220> FEATURE:
<223> OTHER INFORMATION: Synthetic sequence

<400> SEQUENCE: 2

```
Met Gln Asn Pro Gln Gly Gln Gln Gln Gln Gln Gln Gln Gln Gln Gln
1               5                   10                  15

Asn Pro Pro Gln Asn Asn Ala Gly Gly Asn Gly Ser Ser Gln Asn Phe
            20                  25                  30

Phe Val Asn Glu Ile Tyr Ala Asn Pro Lys Phe Ile Glu Glu Ile Asp
        35                  40                  45

Ser Ser Ile Ala Lys Leu Asp Gly Glu Leu Lys Gly Lys Ala Glu Lys
    50                  55                  60

Val Lys Ser Val Pro Thr Ala Val Trp Leu Ala Trp Glu Gly Ala Pro
65                  70                  75                  80

Ala Glu Val Glu Gln His Leu Lys Ala Ala Gly Ser Lys Thr Val Val
                85                  90                  95

Phe Ile Leu Tyr Met Ile Pro Thr Arg Asp Cys Asn Ser Leu Ala Ser
            100                 105                 110

Ala Gly Gly Ala Ser Ser Leu Glu Thr Tyr Lys Gly Tyr Ile Asp Ser
        115                 120                 125

Ile Ser Asn Thr Ile Lys Ser Tyr Pro Ser Ser Lys Val Val Met Val
    130                 135                 140

Val Glu Pro Asp Thr Leu Gly Asn Leu Val Thr Gly Thr Ser Glu Ser
145                 150                 155                 160

Cys Lys Thr Val His Thr Met His Lys Asn Ala Leu Ser Tyr Ala Val
                165                 170                 175

Asn Val Phe Gly Ala Met Ser Asn Val Ser Val Tyr Leu Asp Ala Ala
            180                 185                 190

His Gly Lys Trp Leu Gly Gly Val Thr Asp Lys Val Ala Ala Val Ile
        195                 200                 205

Lys Glu Ile Leu Ser Asn Ala Pro Asn Gly Lys Ile Arg Gly Val Ser
    210                 215                 220

Thr Asn Val Ser Asn Tyr Gln Pro Val Ala Ser Glu Tyr Ser Tyr His
225                 230                 235                 240

Gln Lys Leu Ala Ser Ser Leu Ser Ala Val Gly Ile Ser Asp Ile His
                245                 250                 255

Phe Ile Val Asp Thr Gly Arg Asn Gly Val Asp Ile Thr Glu Ala Phe
            260                 265                 270

Ser Lys Thr Glu Thr Trp Cys Asn Phe Ile Gly Thr Gly Phe Gly Glu
        275                 280                 285
```

-continued

| | | | | | | | | | | | | | | |
|---|---|---|---|---|---|---|---|---|---|---|---|---|---|---|
| Arg | Pro | Lys | Gly | Asn | Pro | Asn | Pro | Gly | Met | Pro | Leu | Leu | Asp | Ala | Tyr |
| | 290 | | | | 295 | | | | 300 | | | | | | |
| Met | Trp | Leu | Lys | Thr | Pro | Gly | Glu | Ala | Asp | Gly | Ser | Ser | Thr | Gly | Ser |
| 305 | | | | | 310 | | | | | 315 | | | | | 320 |
| Arg | Ala | Asp | Pro | Val | Cys | Ala | Arg | Ala | Asp | Ser | Leu | Pro | Gly | Ser | Pro |
| | | | | 325 | | | | | 330 | | | | | 335 | |
| Asp | Ala | Gly | Gln | Trp | Phe | His | Glu | Tyr | Phe | Val | Gln | Leu | Leu | Lys | Asn |
| | | | 340 | | | | | 345 | | | | | 350 | | |
| Ala | Lys | Pro | Gly | Phe | | | | | | | | | | | |
| | | 355 | | | | | | | | | | | | | |